(12) United States Patent
Rao et al.

(10) Patent No.: US 10,876,902 B2
(45) Date of Patent: Dec. 29, 2020

(54) POSITION-CONTROLLED THERMOCOUPLE

(71) Applicant: Biosense Webster (Israel) Ltd.

(72) Inventors: Anand Rao, Tustin, CA (US); Thomas Selkee, Claremont, CA (US); Keshava Datta, Chino Hills, CA (US); Thanh Nguyen, El Monte, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 234 days.

(21) Appl. No.: 15/867,457

(22) Filed: Jan. 10, 2018

(65) Prior Publication Data

US 2019/0212206 A1  Jul. 11, 2019

(51) Int. Cl.
| G01K 7/00 | (2006.01) |
|---|---|
| G01K 1/00 | (2006.01) |
| G01K 7/02 | (2006.01) |
| A61B 18/14 | (2006.01) |
| G01K 13/00 | (2006.01) |
| G01K 1/02 | (2006.01) |
| A61B 18/00 | (2006.01) |

(52) U.S. Cl.
CPC ............ *G01K 7/02* (2013.01); *A61B 18/1492* (2013.01); *G01K 1/026* (2013.01); *G01K 13/002* (2013.01); *A61B 2018/00023* (2013.01); *A61B 2018/00029* (2013.01); *A61B 2018/00351* (2013.01); *A61B 2018/00577* (2013.01); *A61B 2018/00797* (2013.01); *A61B 2018/00821* (2013.01); *A61B 2018/00988* (2013.01); *A61B 2018/1472* (2013.01); *A61B 2218/002* (2013.01); *G01K 2213/00* (2013.01)

(58) Field of Classification Search
USPC .................. 374/179, 166, 208, 110; 600/549
See application file for complete search history.

(56) References Cited

U.S. PATENT DOCUMENTS

| 5,391,199 | A | | 2/1995 | Ben-Haim | |
|---|---|---|---|---|---|
| 5,810,802 | A | * | 9/1998 | Panescu | A61B 5/0422 374/E1.005 |
| 5,991,650 | A | * | 11/1999 | Swanson | A61B 5/0422 374/E1.005 |
| 6,045,550 | A | * | 4/2000 | Simpson | A61B 18/1492 600/549 |
| 6,162,184 | A | | 12/2000 | Swanson et al. | |
| 6,197,021 | B1 | * | 3/2001 | Panescu | A61B 5/0422 374/E1.005 |
| 6,239,724 | B1 | | 5/2001 | Doron et al. | |

(Continued)

FOREIGN PATENT DOCUMENTS

| EP | 3020355 | 5/2016 |
|---|---|---|
| WO | 96/05768 | 2/1996 |

OTHER PUBLICATIONS

European Search Report and Opinion for European Patent Application No. 19150989.2; dated Jun. 5, 2019.

*Primary Examiner* — Mirellys Jagan
(74) *Attorney, Agent, or Firm* — Dergosits & Noah LLP; Todd A. Noah

(57) ABSTRACT

A thermocouple assembly may feature a plurality of temperature sensors formed by thermocouple junctions. The sensors may be disposed upon a positioner, that has a configuration that displaces each of the plurality of temperature sensors from a longitudinal axis of the positioner.

14 Claims, 7 Drawing Sheets

(56) References Cited

U.S. PATENT DOCUMENTS

| | | | |
|---|---|---|---|
| 6,312,425 B1* | 11/2001 | Simpson | A61B 18/1492 600/549 |
| 6,332,089 B1 | 12/2001 | Acker et al. | |
| 6,468,260 B1 | 10/2002 | Bumbalough et al. | |
| 6,484,118 B1 | 11/2002 | Govari | |
| 6,500,167 B1 | 12/2002 | Webster, Jr. | |
| 6,522,933 B2 | 2/2003 | Nguyen | |
| 6,618,612 B1 | 9/2003 | Acker et al. | |
| 6,690,963 B2 | 2/2004 | Ben-Haim et al. | |
| 7,729,742 B2 | 6/2010 | Govari | |
| 8,437,832 B2 | 5/2013 | Govari et al. | |
| 8,617,087 B2 | 12/2013 | Schultz | |
| 9,675,411 B2 | 6/2017 | Govari et al. | |
| 2002/0048310 A1* | 4/2002 | Heuser | A61B 5/01 374/141 |
| 2002/0077564 A1* | 6/2002 | Campbell | A61B 5/01 600/549 |
| 2002/0082515 A1* | 6/2002 | Campbell | A61B 5/01 600/549 |
| 2002/0111560 A1* | 8/2002 | Kokate | A61B 5/01 600/549 |
| 2003/0176810 A1* | 9/2003 | Maahs | A61B 5/01 600/549 |
| 2004/0059244 A1* | 3/2004 | Flores | A61B 5/015 600/549 |
| 2004/0068178 A1 | 4/2004 | Govari | |
| 2004/0176699 A1* | 9/2004 | Walker | A61B 5/015 600/549 |
| 2006/0015092 A1* | 1/2006 | Joye | A61B 1/00082 606/21 |
| 2008/0161788 A1 | 7/2008 | Dando et al. | |
| 2010/0030098 A1* | 2/2010 | Fojtik | A61B 5/015 600/549 |
| 2010/0067562 A1* | 3/2010 | Wakabayashi | G01K 1/14 374/208 |
| 2011/0130648 A1 | 6/2011 | Beeckler et al. | |
| 2012/0250726 A1* | 10/2012 | Sorkine | G01K 7/028 374/179 |
| 2014/0171821 A1* | 6/2014 | Govari | A61M 25/0009 600/549 |
| 2014/0171936 A1 | 6/2014 | Govari et al. | |
| 2014/0276052 A1* | 9/2014 | Rankin | A61B 18/1492 600/439 |
| 2014/0276124 A1* | 9/2014 | Cholette | A61B 5/01 600/483 |
| 2015/0335263 A1* | 11/2015 | Srivastava | A61B 5/065 600/587 |
| 2015/0342671 A1* | 12/2015 | Govari | A61B 18/1492 600/549 |
| 2016/0128765 A1* | 5/2016 | Schultz | A61B 18/1492 606/41 |
| 2019/0212207 A1* | 7/2019 | Rao | A61B 18/1492 |
| 2019/0212208 A1* | 7/2019 | Rao | A61B 18/1492 |
| 2020/0030024 A1* | 1/2020 | Rao | A61N 1/056 |
| 2020/0206466 A1* | 7/2020 | Nguyen | A61B 18/1492 |

* cited by examiner

US 10,876,902 B2

POSITION-CONTROLLED THERMOCOUPLE

FIELD OF THE PRESENT DISCLOSURE

This disclosure relates generally to methods and devices for percutaneous medical treatment, and specifically to catheters that have temperature sensing capabilities, such as ablation catheters. More particularly, this disclosure relates to a thermocouple assembly for use in such catheters that provides more accurate temperature sensing at multiple locations.

BACKGROUND

Radiofrequency (RF) electrode catheters have been in common use in medical practice for many years. They are used to stimulate and map electrical activity in the heart and to ablate sites of aberrant electrical activity. Specifically, targeted ablation may be performed for a number of indications. For example, ablation of myocardial tissue is well known as a treatment for cardiac arrhythmias by using a catheter to apply RF energy and create a lesion to break arrhythmogenic current paths in the cardiac tissue. As another example, a renal ablation procedure may involve the insertion of a catheter having an electrode at its distal end into a renal artery in order to complete a circumferential lesion in the artery in order to denervate the artery for the treatment of hypertension.

In such procedures, a reference electrode is typically provided and may be attached to the skin of the patient or by means of a second catheter. RF current is applied to the tip electrode of the ablating catheter, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the target tissue resulting in formation of a lesion which is electrically non-conductive. The lesion may be formed in tissue contacting the electrode or in adjacent tissue. During this process, heating of the electrode also occurs as a result of conduction from the heated tissue to the electrode itself.

As will be appreciated, it is desirable to employ catheters that can sense temperature to help guide the procedure, such as by offering an indication when an efficient ablation temperature has been reached or by reducing conditions under which tissue may be overheated. When the electrode reaches critical temperatures, denaturation of blood proteins causes coagulum formation. Impedance can then rise and limit current delivery. Within tissue, overheating can cause steam bubble formation (steam "pops") with risk of uncontrolled tissue destruction or undesirable perforation of bodily structures. Although ablation catheters may be irrigated to provide greater control over the temperature of catheter components and the surrounding tissue, it is still important to accurately monitor temperature at multiple locations. Indeed, the flow of irrigation fluid may be tailored in part based on feedback from the temperature sensors. For example, Biosense Webster Inc. (Diamond Bar, Calif.) offers the ThermoCool® irrigated-tip catheter for use with its CARTO® integrated mapping and ablation system. The metal catheter tip, which is energized with radio-frequency (RF) electrical current to ablate the tissue, has a number of peripheral holes, distributed circumferentially around the tip, for irrigation of the treatment site. A pump coupled to the catheter delivers saline solution to the catheter tip, and the solution flows out through the holes during the procedure in order to cool the catheter tip and the tissue. Representative details concerning irrigated ablation catheters may be found in commonly-owned U.S. Pat. No. 9,675,411, whose disclosure is incorporated herein by reference in its entirety.

While ablation catheters have been discussed as being a representative example, one of ordinary skill in the art will recognize that many types of intravascular devices may benefit from improved temperature sensing capabilities. Accordingly, it would be desirable to provide a thermocouple assembly design that may be used with an ablation catheter or other intravascular device that allows sensing of temperature at multiple locations to provide more accurate temperature measurement. Further, it would be desirable to improve the response time of the temperature sensing. As will be described in the following materials, this disclosure satisfies these and other needs.

SUMMARY

The present disclosure is directed to a thermocouple assembly for use with an electrode, comprising a plurality of temperature sensors formed by thermocouple junctions and a positioner. The plurality of temperature sensors may be disposed upon the positioner and the positioner may have a configuration that displaces each of the plurality of temperature sensors from a longitudinal axis of the positioner.

In one aspect, the plurality of temperature sensors may include a proximal sensor and a distal sensor. At least one additional temperature sensor may be positioned between the proximal sensor and the distal sensor.

In one aspect, the positioner may be PEEK.

In one aspect, the positioner may have a track to receive the plurality of temperature sensors and leads connecting to the plurality of temperature sensors. The positioner may have projections extending from opposing sides of the track to retain the leads. The positioner may have a stop at a distal end of the track.

In one aspect, the thermocouple assembly may be secured to an electrode. The thermocouple assembly may be disposed within a longitudinal bore of the electrode. The displacement of each of the plurality of temperature sensors may be in a direction towards a nearest outer surface of the electrode. The displacement of each of the plurality of temperature sensors may be in a direction away from a longitudinal axis of the electrode. The displacement of each of the plurality of temperature sensors may cause the thermocouple assembly to be held in contact with a surface of the longitudinal bore opposing the nearest outer surface of the electrode.

In one aspect, the electrode may have a cavity for supplying irrigation fluid to apertures in an outer surface of the electrode so that the displacement of each of the plurality of temperature sensors may be in a direction away from the cavity.

In one aspect, the displacement of each of the plurality of temperature sensors may form at least one air gap between at least one of the plurality of temperature sensors and a surface of the longitudinal bore opposing the longitudinal axis of the electrode.

This disclosure is also directed to a method for forming a thermocouple assembly. The method may include creating a plurality of temperature sensors with thermocouple junctions and disposing the plurality of temperature sensors upon a positioner, wherein the positioner may have a configuration that displaces each of the plurality of temperature sensors from a longitudinal axis of the positioner.

In one aspect, the thermocouple assembly may be secured to an electrode, which may include disposing the thermocouple assembly within a longitudinal bore of the electrode. The thermocouple assembly may be temporarily deformed before disposing the thermocouple assembly within a longitudinal bore of the electrode.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains.

Finally, as used in this specification and the appended claims, the singular forms "a", "an" and "the" include plural referents unless the content clearly dictates otherwise.

Figure 1:
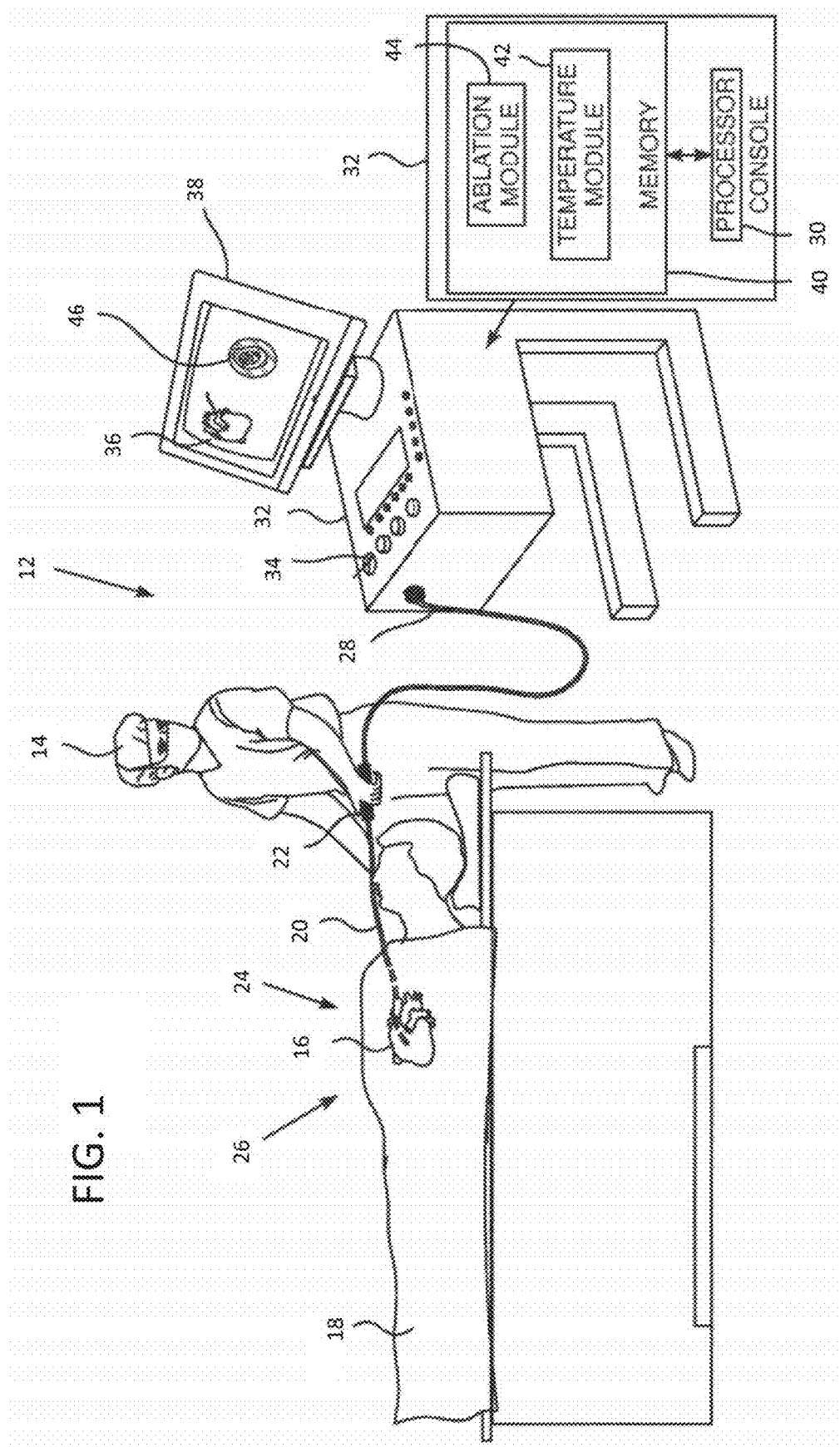
FIG. 1 is a schematic view of an ablation system in accordance with an embodiment of the present invention.

FIG. 1 is a schematic illustration of an invasive medical procedure using system 12, according to an embodiment of the present invention. The procedure is performed by a medical professional 14, and, by way of example, the procedure in the description hereinbelow is assumed to comprise ablation of a portion of a myocardium 16 of the heart of a human patient 18. However, it will be understood that embodiments of the present invention are not just applicable to this specific procedure, and may include substantially any procedure on biological tissue or on non-biological material.

In order to perform the ablation, professional 14 inserts a catheter 20 into a lumen of the patient, using handle 22, so that a distal end 24 of the catheter enters the heart of the patient. Distal end 24 comprises at least a tip electrode 26 for contacting locations of the myocardium. Catheter 20 has a proximal end 28 for connection to associated equipment as described below. Distal end 24 of the catheter is described in more detail with reference to FIGS. 3A, 3B and 3C.

System 12 is controlled by a system processor 30, which is located in an operating console 32 of the system. Console 32 comprises controls 34 which are used by professional 14 to communicate with the processor. During the procedure, processor 30 typically tracks a location and an orientation of distal end 24 of the catheter, using any method known in the art. For example, processor 30 may use a magnetic tracking method, wherein magnetic transmitters external to patient 18 generate signals in coils positioned in the distal end. The CARTO® system referenced above uses such a tracking method and additional details may be found in U.S. Pat. Nos. 5,391,199, 6,484,118, 6,239,724, 6,618,612, 6,332,089, 6,690,963, 7,729,742, in PCT Patent Publication WO 96/05768, and in U.S. Patent Publication No. 2004/0068178 A1, whose disclosures are all incorporated herein by reference.

The software for processor 30 may be downloaded to the processor in electronic form, over a network, for example. Alternatively or additionally, the software may be provided on non-transitory tangible media, such as optical, magnetic, or electronic storage media. The track of distal end 24 is typically displayed on a three-dimensional representation 36 of the heart 16 of patient 18 on a screen 38. In order to operate system 12, processor 30 communicates with a memory 40, which has a number of modules used by the processor to operate the apparatus. Thus, memory 40 comprises a temperature module 42 and an ablation module 44, for example, and typically comprises other modules, such as a force module for measuring the force on end 24, a tracking module for operating the tracking method used by processor 30, and an irrigation module allowing the processor to control irrigation provided for distal end 24. For simplicity, such other modules, which may comprise hardware as well as software elements, are not illustrated in FIG. 1. Processor 30 typically uses results of measurements of temperature acquired by module 42 to display on screen 38 a temperature distribution map 46.

Figure 2:
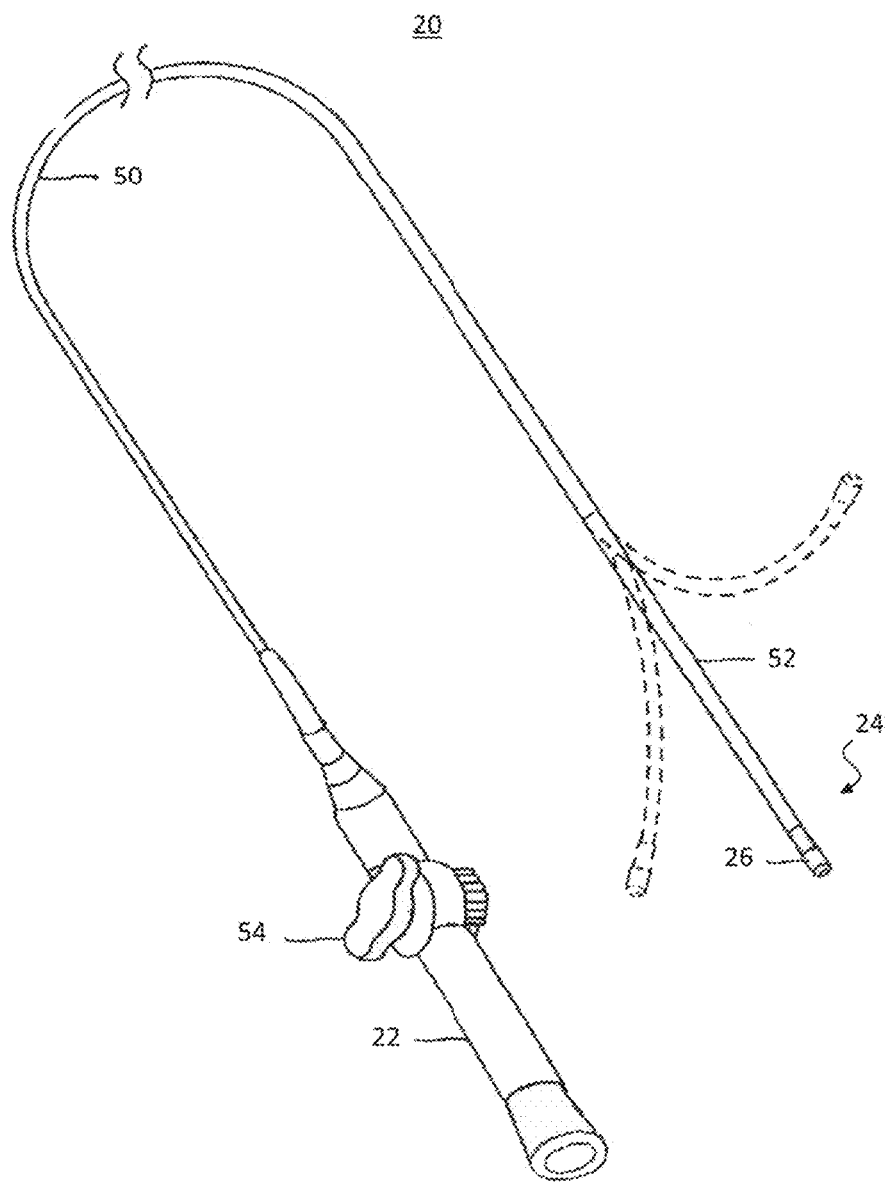
FIG. 2 is a perspective view of a catheter in accordance with an embodiment of the present invention.

A schematic elevational view of catheter 20 is illustrated in FIG. 2, showing an elongated body that includes an insertion shaft or catheter body 50 having a longitudinal axis, and an intermediate section 52 distal of the catheter body that optionally may be uni- or bi-directionally deflectable off-axis from the catheter body as indicated. Proximal of catheter body 50 is control handle 22 that allows an operator to maneuver the catheter as disclosed above, such as by deflecting intermediate section 52 when a steerable embodiment is employed. For example, control handle 22 may include deflection knob 54 that is pivoted in a clockwise or counterclockwise direction for deflection in the respective direction. In other embodiments, other steerable designs may be employed, such as the control handles for manipulating multiple control wires as described, for example, in U.S. Pat. Nos. 6,468,260, 6,500,167, 6,522,933 and 8,617,087, the entire disclosures of which are incorporated herein by reference.

Catheter body 50 is flexible, i.e., bendable, but substantially non-compressible along its length and may be of any suitable construction and made of any suitable material. In one aspect, an outer wall made of polyurethane or PEBAX may have an imbedded braided mesh of stainless steel or the like, as is generally known in the art, to increase torsional stiffness of catheter body 50 so that, when the control handle 22 is rotated, the intermediate section 52 will rotate in a corresponding manner Depending upon the intended use, the outer diameter of catheter body 50 may be approximately 8 french, and in some embodiments, may be 7 french. Likewise, the thickness of the outer wall of catheter body 50 may be thin enough so that a central lumen may accommodate any desired wires, cables and/or tubes, as will be described in further detail below. The useful length of the catheter, i.e., that portion that can be inserted into the body may vary as desired. In exemplary embodiments, the useful length may range from about 110 cm to about 120 cm. The length of the intermediate section 52 may correspond to a relatively small portion of the useful length, such as from about 3.5 cm to about 10 cm, and in some embodiments, from about 5 cm to about 6.5 cm.

Figures 3A, 3B, 3C:
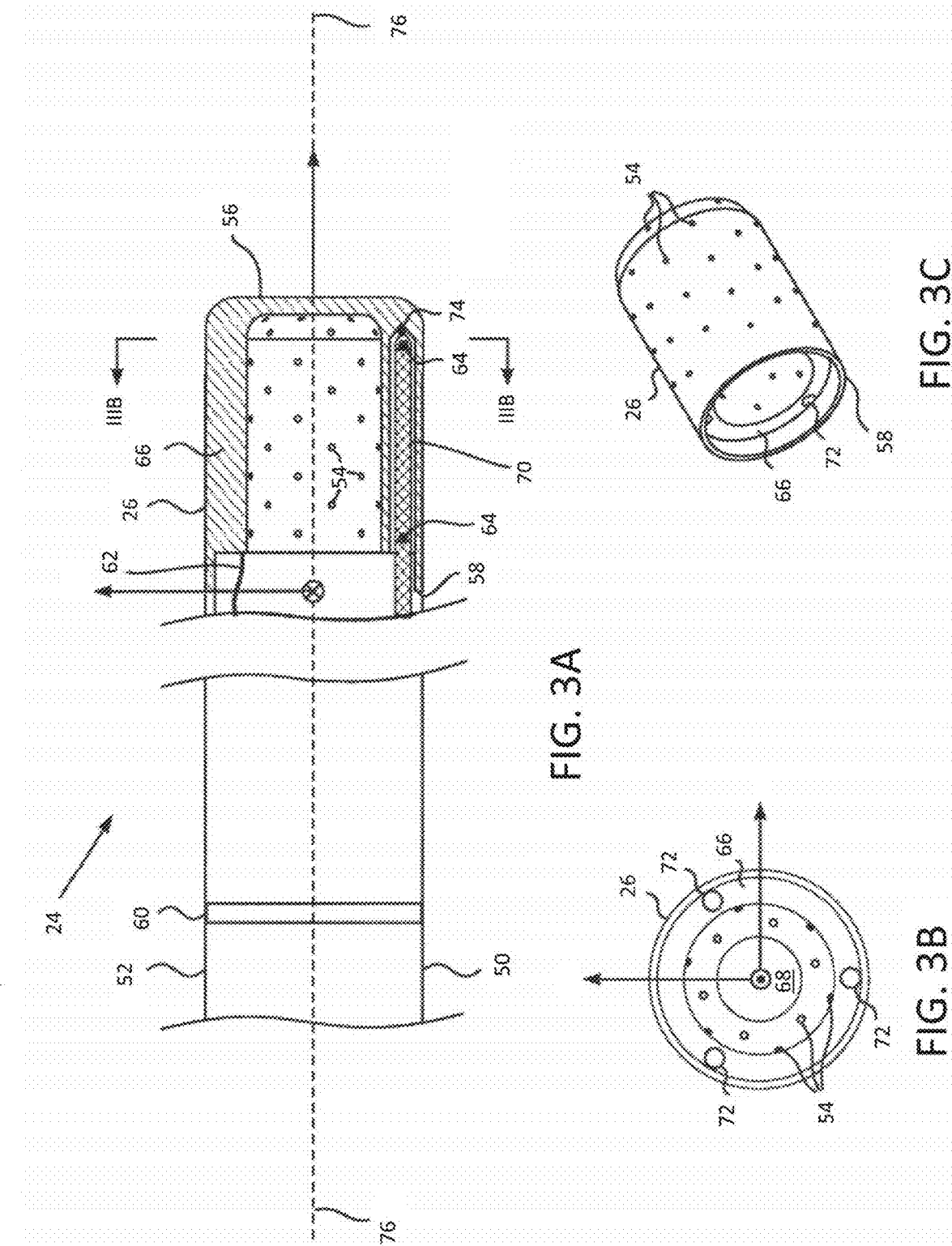
FIGS. 3A, 3B and 3C schematically illustrate a distal end of the catheter of FIG. 1 showing a tip shell electrode with position-controlled thermocouples in accordance with an embodiment of the present invention.

Details regarding one embodiment of the distal end 24 of catheter 20 are illustrated in FIGS. 3A, 3B and 3C. As indicated, electrode 26 is configured as an elongated, generally cylindrical portion with an atraumatic distal portion. The shell of electrode 26 defines an interior cavity that is in fluid communication with a lumen extending the length of catheter body 50 to supply irrigation fluid. A plurality of irrigation apertures 54 are distributed substantially evenly across the surface of electrode 26, through which fluid may exit to outside of the electrode 26, to provide cooling of electrode 26 and the environment adjacent electrode 26 as desired. The shell of electrode 26 may be made of any suitable electrically-conductive material, such as palladium, platinum, gold, iridium and combinations and alloys thereof, including, Pd/Pt (e.g., 80% Palladium/20% Platinum) and Pt/Ir (e.g., 90% Platinum/10% Iridium).

In particular, FIG. 3A is a sectional view along the length of the probe, FIG. 3B is a cross-sectional view along a cut IIIB-IIIB that is marked in FIG. 3A, and FIG. 3C is a perspective view of a section of the distal end. As shown, electrode 26 is positioned distal to intermediate section 52 of the catheter body. Tip electrode 26 may have an approximately planar conducting surface 56 at its distal end and a substantially columnar surface 58 positioned proximally. As desired, additional electrodes, such as electrode 60, may be configured as a ring electrode and may be positioned on intermediate section 52. An electrical conductor 62 conveys radio-frequency (RF) electrical energy from ablation module 44 (FIG. 1), through catheter body 50, to electrode 26, and thus energizes the electrode to ablate myocardial tissue with which the electrode is in contact. Module 44 controls the level of RF power dissipated via electrode 26. During the ablation procedure, cooling fluid flowing out through apertures 54 may irrigate the tissue under treatment.

Temperature sensors 64, comprising thermocouples which are typically copper-constantan thermocouples, and also referred to herein as thermocouples 64, are mounted within tip electrode 26 at locations that are arrayed around the distal tip of the catheter, both axially and circumferentially. This example contains six sensors, with one group of three sensors in a distal location, close to the tip, and another group of three sensors in a slightly more proximal location. This distribution is shown only by way of example, however, and greater or smaller numbers of sensors may be mounted in any suitable locations within the tip electrode 26. Thermocouples 64 are connected by leads (not shown in these views) running through the length of catheter body 50 to provide temperature signals to temperature module 42.

In the disclosed embodiment, tip electrode 26 features a side wall 66 that is relatively thick, on the order of 0.5 mm thick, in order to provide the desired thermal insulation between temperature sensors 64 and the cooling fluid inside a central cavity 68 of the tip. The cooling fluid exits cavity 68 through apertures 54 as noted above. Again, with respect to this embodiment only, sensors 64 are grouped as pairs of proximal and distal thermocouples within three separate position-controlled thermocouple assemblies 70, which are fitted into longitudinal bores 72 in side wall 66. As described in further detail below, thermocouple assemblies 70 may be configured to positionally control and thereby adjust the position of sensors 64 within longitudinal bores 72, and may be held in place at their distal ends by a suitable cement 74, such as epoxy. Notably, thermocouple assembly 70 may position the sensors 64 towards the outer surface of electrode 26, such as surfaces 56 and/or 58. For example, the positioning may cause thermocouple assembly 70 to come into contact with the inner surface of longitudinal bore 72 at a location that substantially directly opposes the outer surface of tip electrode 26 and/or may exert additional force that holds thermocouple assembly 70 in contact, preventing the formation of an air gap that would reduce the thermal response time of sensors 64. In other embodiments, the positioning may reduce presence of such an air gap, particularly with regard to portions of thermocouple assembly 70 adjacent sensors 64.

The arrangement described above provides an array of six sensors 64, but other arrangements, and use of other numbers of sensors, may be employed as desired as will be apparent to those having ordinary skill in the art. All such arrangements and numbers are included within the scope of the present disclosure. Desirably, temperature sensors 64 may be positioned at different locations to measure temperature at the corresponding outer surfaces of electrode 26.

Sensors 64 may be in proximity to and thermal communication with the outer surfaces, for example due to the positional control provided by thermocouple assembly 70, and may be thermally insulated from, rather than immersed in, the cooling irrigation fluid delivered from cavity 68 through apertures 54. The sensors thus provide multiple temperature readings that are substantially independent of the cooling fluid temperature, at different locations on tip electrode 26. The sensor that gives the highest temperature reading may be the one that is in contact with the tissue being ablated, and the temperature measured by this sensor varies linearly with the actual tissue temperature. Flow of the irrigation fluid may be generally lower in areas that are in firm contact with the tissue, and the sensors in these areas typically give the highest temperature readings. In some applications, the reading from the "hottest" sensor may thus be used in particular to monitor the tissue temperature and control the applied power and duration of the ablation procedure in order to obtain the desired therapeutic result without excessive tissue damage. Alternatively or additionally, the temperature readings of the multiple sensors can be combined and interpolated to give a map of temperature over the area of the catheter tip.

In the description herein, distal end 24 is assumed to define a set of xyz orthogonal axes, where an axis 76 of the distal end corresponds to the z axis of the set. For simplicity and by way of example, the y axis is assumed to be in the plane of the paper, the xy plane is herein assumed to correspond to the plane orthogonal to the z axis, and the origin of the xyz axes is assumed to be the center catheter body 50. The positional control of thermocouple assembly 70 may generally be with respect to the relative location of the sensors 64 in the xy plane and perpendicular to axis 76, effectively in the direction of the nearest outer surface of tip electrode 26.

Typically, distal end 24 contains other functional components, which are outside the scope of the present disclosure and are therefore omitted for the sake of simplicity. For example, the distal end of the catheter may contain steering wires, as well as sensors of other types, such as a position sensor and a force sensor. Catheters containing components of these kinds are described, for example, in U.S. Pat. No. 8,437,832 and U.S. Patent Publication No. 2011/0130648, which are incorporated herein by reference.

As discussed above, thermocouple assemblies 70 may be disposed within each longitudinal bore 72. Further details regarding thermocouple assembly 70 may be appreciated in reference to FIG. 4, which schematically shows proximal and distal sensors 64 formed by thermocouple junctions, both of which are coupled to leads 78 for communicating electrical signals to the proximal end of catheter 20. In this embodiment, leads 78 may be configured as a flat, three wire cable, having one common wire and one wire dedicated to each sensor 64. Different numbers of wires may be employed as warranted by the number of sensors being deployed by thermocouple assembly 70. Sensors 64 may be formed by a temperature measuring junction between a pair of leads 78. For example, any insulating covering on leads 78 may be stripped so that they may be soldered together to form the junction. Leads 78, and sensors 64, may be secured to positioner 80 that functions to provide positional control over sensors 64 by disposing them towards the outer surface of electrode 26 as discussed above. For example, positioner 80 may be configured to displace sensors 64 axially with respect to the longitudinal axis of the positioner. Positioner 80 may be injection molded from a polymeric material having a high glass transition temperature (280° F. and above) combined with modulus of elasticity large enough (400,000 psi and above) to provide consistent spring properties without temperature stress relaxation such that the thermocouples are consistently biased against the tip dome outer wall during tip dome ablation procedures. Suitable thermoplastics may include polyether ether ketone (PEEK), polyetherimide (Ultem®) and polyamide-imide (Torlon®). Notably, positioner 80 may have sufficient resilience to be deformed slightly for insertion within longitudinal bore 72, so that a residual force may help bring desired portions of thermocouple assembly 70 into contact with portions of the inner surface of longitudinal bore 72, such as those directly opposing the outer surface of electrode 26.

Figure 4:
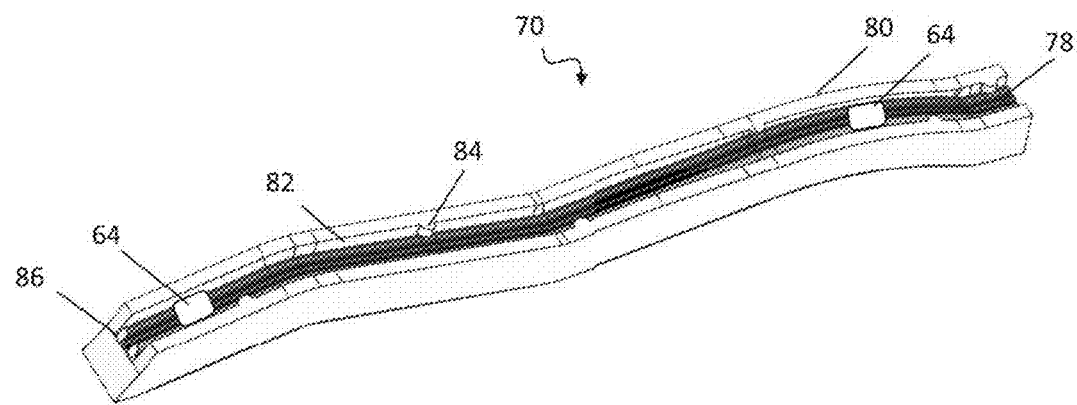
FIG. 4 is a schematic view of a position-controlled thermocouple in accordance with an embodiment of the present invention.
Figure 5:
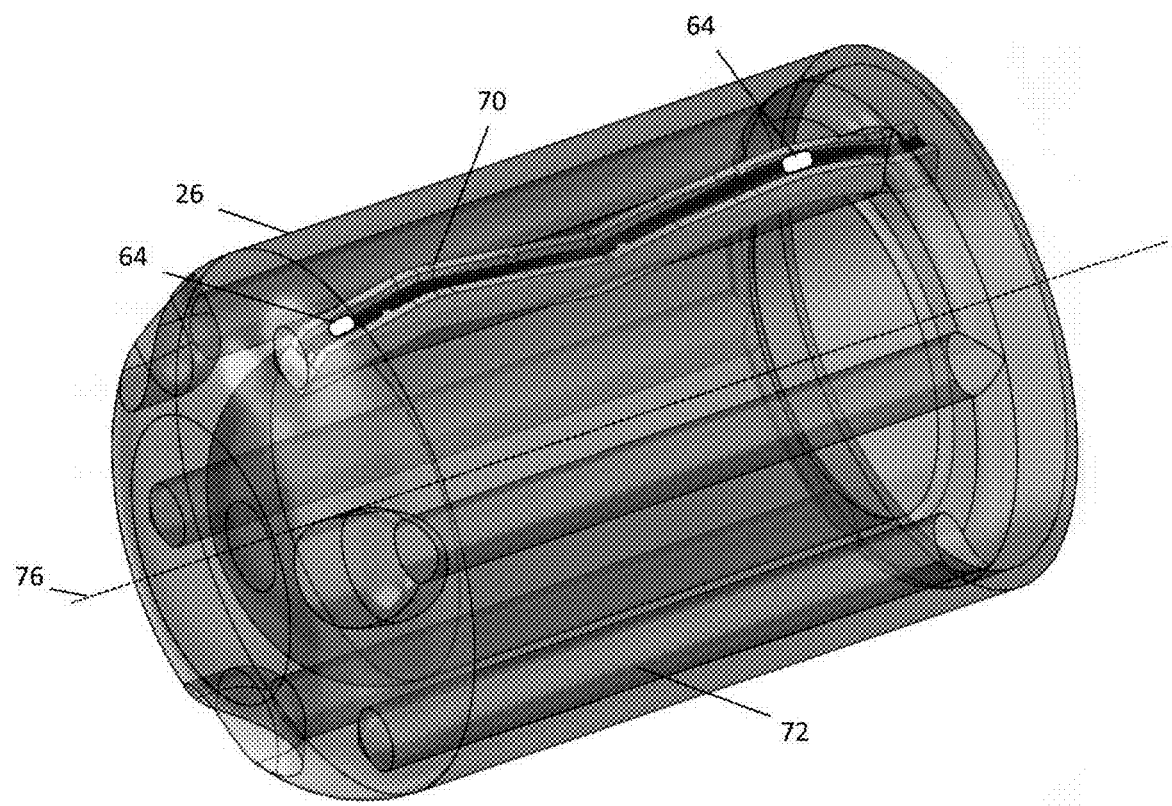
FIG. 5 is a schematic, transparent view of a position-controlled thermocouple within an electrode in accordance with an embodiment of the present invention.

In the embodiment depicted in FIG. 4, positioner 80 has a generally M-shaped profile that may be formed by angled and/or curved portions as shown that provide the displacement of sensors 64 from the longitudinal axis of positioner 80. Positioner 80 may be molded, machined or otherwise manufactured to include a longitudinally oriented track 82 sized to receive leads 78. To help retain leads 78 within track 82, a plurality of projections 84 extend partially into the track to constrain leads 78. The distal end of positioner 80 may have a stop 86, against which leads 78 abut to provide a more reproducible longitudinal positioning of leads 78, and correspondingly, sensors 64. Since positioner 80 may be formed from an electrically insulating material, disposing leads 78 within track 82 may isolate sensors 64 to reduce or prevent shorting with electrode 26. The configuration of thermocouple assembly 70 provides improved temperature response due to the orientation of sensors 64 within longitudinal bore 72 as shown in the schematic, partially transparent view of FIG. 5. Sensors 64 may be positioned on either side of a middle portion of thermocouple assembly 70 that may be configured to contact longitudinal bore 72 at a surface nearest axis 76 so that the configuration of positioner 80, and combined with the high stiffness (minimum elastic modulus value described above) of the polymeric material, position sensors 64 away from axis 76 and towards the surface of longitudinal bore 72 nearest the outer surface of electrode 26 as shown. In the embodiment of FIG. 5, tip electrode 26 may have six longitudinal bores 72, so that if each thermocouple assembly 70 has two sensors 64, an array of twelve sensors may be formed. This embodiment is only for the purpose of illustration and not limitation, as any number of longitudinal bores 72 may be provided as desired.

Figure 6:
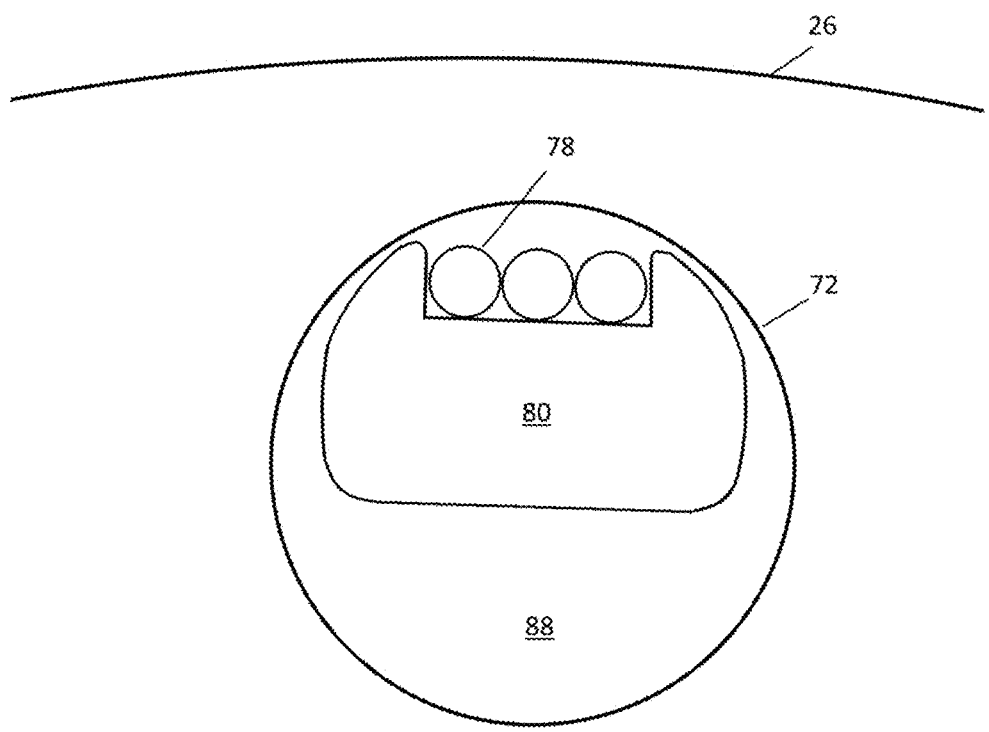
FIG. 6 is a detail view of the cross section of FIG. 3B, showing a position-controlled thermocouple disposed in a longitudinal bore of an electrode in accordance with an embodiment of the present invention.

Additionally, the configuration of thermocouple assembly 70 may also create an air gap 88 between the side of positioner 80 opposing sensors 64 and the surface of longitudinal bore 72 as depicted in FIG. 6, which is a detail view of the cross section shown in FIG. 3B. Since air is a very effective thermal insulator with a thermal conductivity of 0.024 W/m*K, air gap 88 insulates the sensors 64 from the relatively cool irrigation fluid being delivered from cavity 68. Thus, thermocouple assembly 70 positions proximal and distal sensors 64 in contact with the outer shell of electrode 26. As will be appreciated, the techniques of this disclosure help more accurately measure tissue temperature adjacent electrode 26 at the areas corresponding to the positions of sensors 64. Accordingly, thermocouple assembly 70 may more accurately reflect ablation conditions, for example, while exhibiting improved time response. This design also helps reduce the effect of the thermal gradient that may exist caused by the relatively hot side opposing the outer surface of electrode 26 and the relatively cool side opposing cavity 68 when filled with irrigation fluid. Effectively, thermocouple assembly 70 positions sensors 64 within longitudinal bore 72 towards the outer surface of electrode 26 and away from cavity 68. In conventional assemblies that do not feature a positioner embodying the techniques of this disclosure, there may be variability in the relative axial (and longitudinal) position of the sensors between different manufactured units. Accordingly, positioner 80 represents a more reliable and reproducible technique for controlling the position of sensors 64 within longitudinal bore 72, both axially and longitudinally.

Figure 7A:
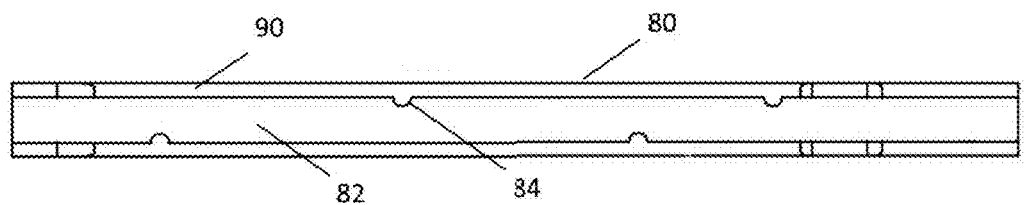
FIGS. 7A, 7B and 7C are schematic top, side and end views, respectively, of the positioner of a position-controlled thermocouple in accordance with an embodiment of the present invention.
Figure 7B:
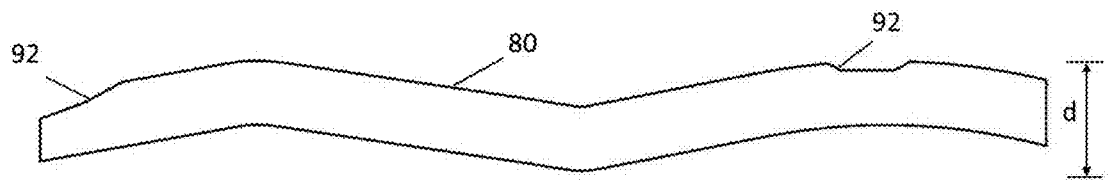
Figure 7C:
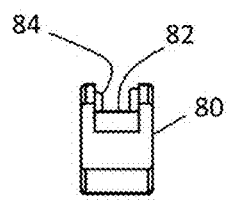

Further details regarding the configuration of positioner 80 may be appreciated in the context of the embodiment shown in FIGS. 7A, 7B and 7C, which show top, side and end views respectively. Representative dimensions regarding this embodiment may include an overall length of approximately 0.110 inches, an overall width of approximately 0.008 inches and a cross-sectional height of approximately 0.007 inches. Track 82 may be defined by opposing rails 90, each having a width of approximately 0.0015 inches and a height of approximately 0.003 inches to provide track 82 with a width of approximately 0.005 inches. Projections 84 may have a width of approximately 0.001 inches. As indicated in FIG. 7B, rails 90 may have cutaways 92 to accommodate sensors 64. In other embodiments, any or all of these dimensions may be adjusted as warranted. In particular, the cross-sectional depth of positioner 80 in conjunction with its profile may define an overall depth d as indicated in FIG. 7B. As will be appreciated, in order to bring sensors 64 into the desired close proximity or contact with the inner surface of longitudinal bore 72, overall depth d may closely correspond to the diameter of longitudinal bore 72. In one aspect, overall depth d may be somewhat larger than the diameter of longitudinal bore 72 so that the resilience of positioner 80 creates a constant spring biasing force holding portions of thermocouple assembly 70 into contact with the surfaces of longitudinal bore 72 as discussed above.

Figure 8:
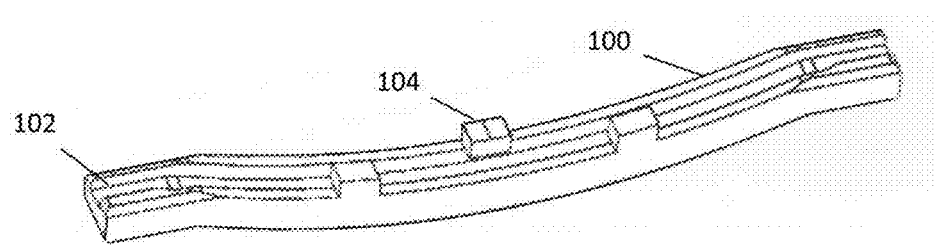
FIG. 8 is a schematic view of an alternate configuration of a positioner e in accordance with an embodiment of the present invention.

In other embodiments, different configurations of positioners may be employed as warranted by the intended application and/or characteristics of the tip electrode in which they are disposed. As an illustrative example only, and without limitation, another embodiment is depicted in FIG. 8, with respect to positioner 100. Here, positioner 100 may have a generally U-shaped configuration, with a curved middle portion and opposing straight portions at either end that may support sensors 64 (not shown in this view) and position them in close proximity or contact with the tip electrode. Similar to the embodiments described above, positioner 100 may have a track 102 configured to receive leads 78. Also similarly, projections 104 may be arrayed on either side of track 102 to mechanically engage and retain leads 78 within the track. In this embodiment, track 102 may not be as deep as leads 78, so projections 104 may extend upwards as well as impinging into the width of track 102.

Figure 9:
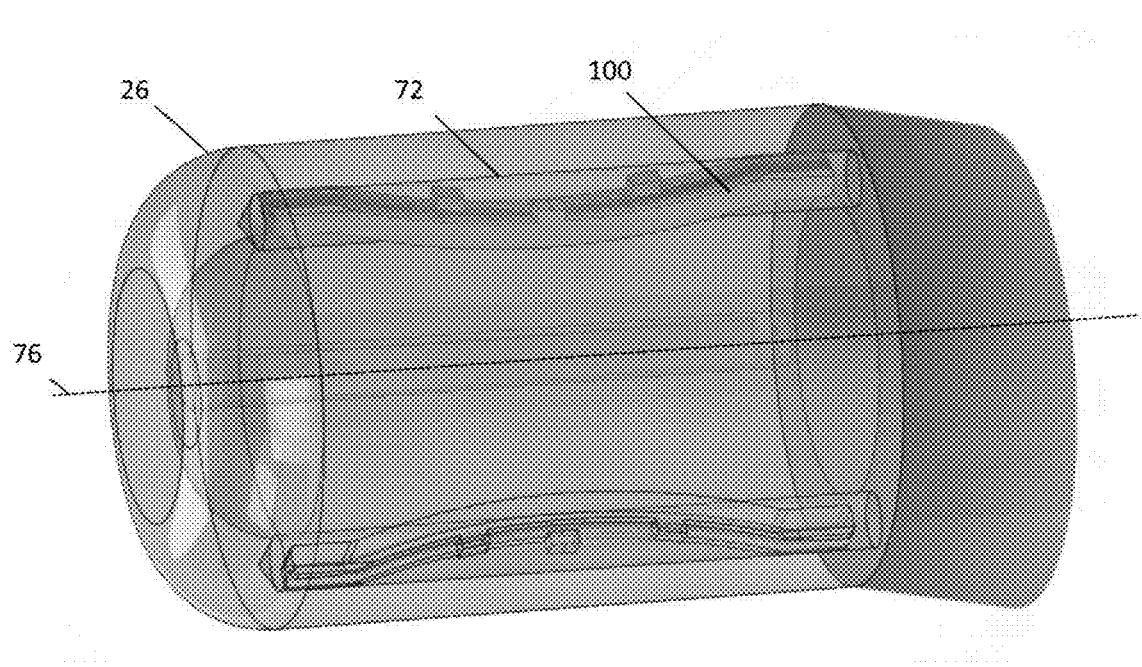
FIG. 9 is a schematic, transparent view of the positioner of FIG. 8 within an electrode in accordance with an embodiment of the present invention.

The relationship of positioner 100 within longitudinal bores 72 of electrode 26 is schematically depicted in the partially transparent view of FIG. 9. Although sensors 64 and leads 78 are not shown in this view for the sake of clarity, it will be appreciated that the positioner is in its nominal configuration that may be designed so that the middle portion of positioner 100 contacts longitudinal bore 72 at a surface nearest axis 76 so that the configuration of positioner 100, and possibly the resilience of polymeric material, places the end portions of positioner 100 away from axis 76 and towards the surface of longitudinal bore 72 nearest the outer surface of electrode 26 as shown. Correspondingly, sensors located on the end portions will be in close proximity or contact with the inner surface of longitudinal bore 72 as desired. Further, these end portions of positioner 100 also create air gaps similar to those described above to help thermally insulate the sensors from the cooling irrigation fluid.

As will be appreciated, the positioners of this disclosure allow sensors 64 to be positioned at different locations along the positioner as desired and depending on the intended application. Importantly, the sensors may be reproducibly located at desired positions along the positioner. Reproducibility is desirable, as a position shift of as little as 0.001 inches may significantly alter the temperature response. Further, the relative longitudinal location of sensors 64 may be tailored as warranted. For example, a distal sensor may be oriented parallel with axis 76, towards surface 56 of electrode 26, and may provide a good representation of tissue temperature during a spot ablation on the myocardial wall, for example, while a proximal sensor may be oriented towards surface 58, generally perpendicularly to axis 76, and may provide a good representation of tissue temperature during radial ablation, such as around the ostium of a heart vessel. Yet other applications may involve 45° ablations, and the positioner may be configured to orient a sensor in that direction.

In other embodiments, the positioner may have any suitable configuration that achieves the desired placement of the plurality of temperature sensors deployed by the thermocouple assembly. Likewise, the configuration of the positioner may reflect the number of sensors being employed so that they are positionally controlled within longitudinal bore 72. Notably, the techniques of this disclosure regarding thermocouple assembly 70 significantly increase thermal conductivity by controlling the position of sensors 64, locating them towards the outer surface of electrode 26 to allow for greater and/or faster temperature response. Moreover, the configuration of thermocouple assembly 70 also helps isolate sensors 64 from cavity 68 and the cooling irrigation fluid through the creation of air gaps 88. Further, sensors 64 may be more reliably placed at their intended positions during manufacture, thereby improving temperature reproducibility and repeatability.

Thus, according to the techniques of this disclosure, thermocouple assembly 70 provides improved temperature response and accuracy, which are important characteristics in completing a successful procedure. For example, procedures known as temperature guided ablation (TGA) involve situations very high power and short duration times, making thermal response a critical characteristic. These techniques also allow for accurate and consistent placement of the thermocouple junctions forming sensors 64 within thermocouple assembly 70, leading to repeatable and reproducible temperature response results. In comparison, conventional techniques do not provide for consistent placement of the sensors relative to the tip electrode, and such catheters suffer from a lack of consistency between units as a result. Moreover, the temperature response of the catheter may not be representative of the tissue temperature during ablation due to suboptimal thermal conductivity and the potential of incorrect placement of the thermocouple junctions within the tip shell. In particular, the variability in position of sensors that are not controlled by a positioner relative to the bore surfaces or other recess of the electrode lead to a propensity for wide variation of sensor orientation with respect to the tip shell. Further, conventional designs that do not adequately isolate the thermocouple junctions from the irrigation fluid and related components exhibit a thermoelectric effect extending across the bore. Temperature differences, or gradients, may influence and average the thermocouple readings when the sensors are inadequately thermally isolated. Without the positional control provided by positioner 80, conventional designs are susceptible to deformation during manufacture, which again can result in variability of positioning of the sensors. These differences in positioning may also lead to different distributions of the volume that is filed with epoxy, again affecting reproducibility, as different thermal responses may be created. Described herein are certain exemplary embodiments. However, one skilled in the art that pertains to the present embodiments will understand that the principles of this disclosure can be extended easily with appropriate modifications to other applications.

What is claimed is:

1. A thermocouple assembly for use with an electrode, comprising a plurality of temperature sensors formed by thermocouple junctions and a positioner, wherein the plurality of temperature sensors are disposed upon the positioner and wherein the positioner has a configuration that radially displaces each of the plurality of temperature sensors from a longitudinal axis of the positioner when the thermocouple assembly is disposed within a longitudinal bore of an electrode, each of the radially displaced temperature sensors being biased into contact with an inner surface of the longitudinal bore.

2. The thermocouple assembly of claim 1, wherein the positioner comprises PEEK.

3. The thermocouple assembly of claim 1, wherein the plurality of temperature sensors comprise a proximal sensor and a distal sensor.

4. The thermocouple assembly of claim 3, further comprising at least one additional temperature sensor positioned between the proximal sensor and the distal sensor.

5. The thermocouple assembly of claim 1, wherein the displacement of each of the plurality of temperature sensors is in a direction towards a nearest outer surface of the electrode.

6. The thermocouple assembly of claim 5, wherein the displacement of each of the plurality of temperature sensors causes the thermocouple assembly to be held in contact with a surface of the longitudinal bore opposing the nearest outer surface of the electrode.

7. The thermocouple assembly of claim 1, wherein the positioner further comprises a track to receive the plurality of temperature sensors and leads connecting to the plurality of temperature sensors.

8. The thermocouple assembly of claim 7, wherein the positioner further comprises projections extending from opposing sides of the track to retain the leads.

9. The thermocouple assembly of claim 7, wherein the positioner further comprises a stop at a distal end of the track.

10. The thermocouple assembly of claim 1, wherein the displacement of each of the plurality of temperature sensors is in a direction away from a longitudinal axis of the electrode.

11. The thermocouple assembly of claim 10, wherein the electrode further comprises a cavity for supplying irrigation fluid to apertures in an outer surface of the electrode and wherein the displacement of each of the plurality of temperature sensors is in a direction away from the cavity.

12. The thermocouple assembly of claim 10, wherein the displacement of each of the plurality of temperature sensors forms at least one air gap between at least one of the plurality of temperature sensors and a surface of the longitudinal bore opposing the longitudinal axis of the electrode.

13. A method for forming a thermocouple assembly, the comprising:
    creating a plurality of temperature sensors with thermocouple junctions;
    disposing the plurality of temperature sensors upon a positioner, wherein the positioner has a configuration that radially displaces each of the plurality of temperature sensors from a longitudinal axis of the positioner; and
    securing the thermocouple assembly to an electrode, wherein securing the thermocouple assembly to the electrode comprises disposing the thermocouple assembly within a longitudinal bore of the electrode, and biasing each of the temperature sensors into contact with an inner surface of the longitudinal bore.

14. The method of claim 13, wherein the thermocouple assembly is temporarily deformed before disposing the thermocouple assembly within the longitudinal bore of the electrode.

* * * * *